US012082790B2

United States Patent
Roxhed et al.

(10) Patent No.: US 12,082,790 B2
(45) Date of Patent: Sep. 10, 2024

(54) BIOPSY/CYTOLOGY DEVICE FOR SAMPLING CELLS OR TISSUE IN MAMMALS

(71) Applicant: Lucky Loop Medical AB, Stockholm (SE)

(72) Inventors: Niclas Roxhed, Bromma (SE); Filipe Marques, Stockholm (SE); Wouter Van Der Wijngaart, Sollentuna (SE); Francisco Baldaque Silva, Stockholm (SE); Urban Arnelo, Huddinge (SE)

(73) Assignee: LUCKY LOOP MEDICAL AB, Stockholm (SE)

( * ) Notice: Subject to any disclaimer, the term of this patent is extended or adjusted under 35 U.S.C. 154(b) by 0 days.

(21) Appl. No.: 18/072,596

(22) Filed: Nov. 30, 2022

(65) Prior Publication Data
US 2023/0099335 A1    Mar. 30, 2023

Related U.S. Application Data

(63) Continuation of application No. PCT/SE2021/051302, filed on Dec. 21, 2021.

(30) Foreign Application Priority Data

Dec. 25, 2020   (SE) .................................. 2030377-2

(51) Int. Cl.
*A61B 10/02* (2006.01)
*A61B 90/00* (2016.01)

(52) U.S. Cl.
CPC .......... *A61B 10/0283* (2013.01); *A61B 90/39* (2016.02); *A61B 2090/3925* (2016.02)

(58) Field of Classification Search
CPC ................ A61B 10/0283; A61B 10/04; A61B 2010/0216; A61B 17/22; A61B 17/221; A61B 2017/320008; A61B 2017/320012
See application file for complete search history.

(56) References Cited

U.S. PATENT DOCUMENTS 2,767,703 A    10/1956  Nieburgs
3,828,790 A  *  8/1974  Curtiss ............. A61B 17/32056
                                                                30/116

(Continued)

FOREIGN PATENT DOCUMENTS

WO    2018/053402 A1    3/2018

OTHER PUBLICATIONS

International Search Report from corresponding International Application No. PCT/SE2021/051302, mailed on Mar. 22, 2022, 4 pages.

*Primary Examiner* — Devin B Henson
(74) *Attorney, Agent, or Firm* — Tucker Ellis LLP

(57) ABSTRACT

A device for detaching cells or tissue from a cavity in a subject, the device includes: an elongated member arranged to be moved within a lumen of a needle or a catheter; and at least one flexible member arranged at a distal end of the elongated member, wherein the flexible member is configured to be brought between a first, constrained configuration within the lumen of the needle or catheter, and a second, expanded configuration outside said lumen, wherein the flexible member in the second, expanded configuration is configured to conform to an inner geometry of a cavity in which the device is inserted.

21 Claims, 10 Drawing Sheets

(56) References Cited

U.S. PATENT DOCUMENTS

| | | | |
|---|---|---|---|
| 5,092,345 A | 3/1992 | Sakita | |
| 2004/0260199 A1* | 12/2004 | Hardia, Jr. | A61B 10/0233 |
| | | | 600/569 |
| 2010/0298736 A1 | 11/2010 | Levy | |
| 2013/0184738 A1* | 7/2013 | Laroya | A61B 17/221 |
| | | | 606/200 |
| 2014/0276204 A1* | 9/2014 | Keady | A61B 10/0233 |
| | | | 600/567 |
| 2014/0276407 A1 | 9/2014 | Devries | |
| 2018/0360481 A1 | 12/2018 | Bonadio | |

* cited by examiner

US 12,082,790 B2

BIOPSY/CYTOLOGY DEVICE FOR SAMPLING CELLS OR TISSUE IN MAMMALS

RELATED APPLICATION DATA

This application is a continuation of International Patent Application No. PCT/SE2021/051302, filed Dec. 21, 2021, which claims the benefit of Swedish Patent Application No. 2030377.2, filed Dec. 25, 2020, the disclosures of which are incorporated herein by reference in their entireties.

TECHNICAL FIELD

The present disclosure generally relates to a device for detaching cells in a cavity of a subject and a liquid biopsy/cytology method to sample cells or tissue from a cavity in a subject. The biopsy/cytology method involves introducing and maneuvering the device via a hollow catheter or needle to enable obtaining a cell sample.

Background Art

Pancreatic cancer is currently the fourth leading cause of cancer-related deaths in the West, and its prevalence is estimated to be the second highest of all cancers by 2030. The prognosis remains very poor, with a 5-year survival rate of only 2%-9%, the lowest among all cancers, due to an advanced disease stage at the time of diagnosis. Pancreatic cystic lesions are precursors of most pancreatic cancers and are present in up to 40% of the general population. Hence, there is a large need to properly diagnose pancreatic cysts according to their benign or malign potential.

Endoscopic ultrasound (EUS) guided fine-needle aspiration (FNA) of cystic lesions, followed by liquid cell analysis, has been used as a diagnostic tool for differentiating benign, potentially malignant, and malignant pancreatic cysts. Whereas results from EUS-FNA of solid lesions are encouraging, those from cystic lesions are dismal due to the scarce cell content in the cystic fluid. The reason for this cell scarcity is that EUS-FNA removes the fluid content of the cysts instead of its lining or wall that is usually covered by cells. The resulting sensitivity of this method ranges from 65% to 95% and the specificity from 50% to 100%. The mean accuracy is 85%, resulting in inconclusive or ambiguous situations in 20% of cases. This lack of information creates situations where cytopathologists are unable to perform a diagnosis. Attempts to tackle this problem were developed with a "through-the-needle" cytologic brush (EchoBrush; Cook Endoscopy, Winston-Salem NC) for operation through 19G needles, which presented diagnostic material in 85.1% of cases. However, increased risk of bleeding led to the discontinued production of these devices.

WO 2018/053402 A1 discloses a pancreatic cyst device deployable through a 22-gauge endoscopic ultrasound (EUS) needle into a cyst. The device is a flexible shaft having a "Spiral Q" shaped distal end designed to conform to the shape of the cyst maximizing contact area and a proximal end which may be connected to a handle allowing an operator to rotate the device within the pancreatic cyst to dislodge cells from the cystic lining.

However, the previously mentioned device still risks injuring the cystic lining and the spiral shaped distal end may break during operation and retraction into the outer shaft. Additionally, the whole length of the flexible shaft is made from Nitinol and is therefore expensive to manufacture.

Thus, there is a need to improve the known devices and methods to overcome the disadvantages mentioned above.

SUMMARY OF INVENTION

An object of the present invention is therefore to achieve a minimally invasive biopsy/cytology device and method which reduces tissue damage at the site of sampling whilst increasing the number of harvested cells or tissue from a cavity in a subject.

This objected is achieved in a first aspect of the present disclosure in which there is provided a device for detaching cells or tissue from a cavity in a subject, the device comprising: an elongated member arranged to be moved within a lumen of a needle or a catheter; and at least one flexible member arranged at a distal end of the elongated member, wherein the flexible member is configured to be brought between a first, constrained configuration within the lumen of the needle or catheter, and a second, expanded configuration outside said lumen, wherein the flexible member in the second, expanded configuration is configured to conform to an inner geometry of a cavity in which the device is inserted.

By providing a device with an elongated member and a flexible member arranged at a distal end thereof, the latter being configured to adopt a shape which conforms to an inner geometry of a cavity in which the device is inserted, it is possible to increase the number of harvested cells in a sampling procedure whilst reducing the risk of damaging tissue at the sampling site.

In one embodiment, the flexible member is a superelastic wire, preferably made of a shape-memory alloy. Superelasticity, especially shape-memory alloys such as nickel titanium, allows the flexible member to adopt the desired shape of the inner geometry of the cavity, e.g. a cyst, when the device is inserted therein.

In one embodiment, the flexible member is arranged to form at least one loop in the expanded configuration. The loop shape allows the flexible member to conform to the desired shape of the inner geometry of the cavity in a simple manner. Additionally, the loop shape reduces the distance required to advance the elongated member before reaching the fully deployed expanded configuration of the flexible member.

In one embodiment, at least a portion of the flexible member has a substantially helical shape in which the axis of the helix is substantially parallel to a general extension direction of the flexible member. The helical shape provides a rough edge to facilitate scraping of cells from the inner lining/wall of the cavity.

In one embodiment, at least a portion of the flexible member has a jagged structure, e.g. exhibiting a plurality of teeth. Preferably, the jagged structure is achieved by means of a microstructure machined or arranged on a surface of the flexible member. The jagged structure provides a rough edge to increase abrasiveness and facilitate scraping of cells from the inner lining/wall of the cavity, thereby increasing the cell yield.

In one embodiment, the elongated member and the flexible member are integrally formed as a monolithic structure, wherein a diameter of the flexible member is smaller than a diameter of the elongated member. The smaller diameter of the flexible member allows it to be doubled up in the constrained configuration, thus reducing the distance required to advance the elongated member before reaching the fully deployed expanded configuration of the flexible member.

In one embodiment, the elongated member comprises a mounting interface at the distal end thereof, and the at least one flexible member is attached to the elongated member by means of the mounting interface. This configuration allows the flexible member to be manufactured separately from the elongated member, e.g. in a different material or using a different process.

In one embodiment, the mounting interface comprises at least one hole for fastening the at least one flexible member to the elongated member, a welding seam, a gluing seam or a mechanical interlocking mechanism between the elongated member and the at least one flexible member, or combinations thereof. Different alternatives for fastening may be selected depending on the desired characteristics and/or expected operating conditions of the device. Preferably, the mounting interface is covered with a heat shrinking tube. The heat shrinking tube protects the mounting interface to prevent rupture or detachment of the flexible member from the elongated member.

In one embodiment, the device further comprises a tubular sheath arranged outside the elongated member and configured to be moved along the elongated member inside the lumen of the needle or catheter. The tubular sheath protects the flexible member from breakage during advancement, operation and retraction in relation to e.g. a hollow needle in which the device is inserted. Preferably, the tubular sheath is made of a polymer such as polyether, polyamide, polyimide or polytetrafluoroethylene, PTFE, or a metal such as nickel titanium or stainless steel.

In one embodiment, the elongated member and/or the flexible member is surface treated or coated to reduce the coefficient of friction.

In a second aspect of the present disclosure, there is provided a device for performing fine-needle aspiration, FNA, or fine-needle biopsy, FNB, the device comprising: a hollow needle; a device according to the first aspect movably arranged inside the lumen of the needle.

In a third aspect of the present disclosure, there is provided a method for performing fine-needle aspiration, FNA, or fine-needle biopsy, FNB to sample cells or tissue from a cavity in a subject comprising:
  providing a hollow needle and a device comprising an elongated member arranged to be moved within a lumen of the needle, and at least one flexible member arranged at the distal end of the elongated member, wherein the flexible member is configured to be brought between a first, constrained configuration within the lumen of the needle, and a second, expanded configuration outside said lumen, wherein the flexible member in the second, expanded configuration is configured to conform to an inner geometry of a cavity in which the device is inserted;
  introducing the needle into the cavity in the subject;
  advancing the elongated member through the lumen of the needle such that the flexible member protrudes from a distal tip of the needle and assumes the second, expanded configuration inside the cavity and comes into contact with an inner wall of the cavity;
  rotating the elongated member such that the expanded flexible member scrapes the inner wall of the cavity;
  retracting the elongated member into the lumen of the needle such that the flexible member is brought to the first, constrained configuration and re-enters the distal tip of the needle;
  aspirating fluid from the cavity through the lumen of the needle; and
  retracting the needle from the cavity.

In one embodiment, the device comprises a tubular sheath arranged outside the elongated member and configured to be moved along the elongated member inside the lumen of the needle or catheter, and the method further comprises:
  before the step of rotating the elongated member, advancing the tubular sheath through the needle such that a distal end of the tubular sheath exits the distal tip of the needle and contacts the expanded flexible member; and
  after the step of retracting the elongated member, retracting the tubular sheath into the needle.

In one embodiment, the step of introducing the needle into the cavity in the subject is performed by means of endoscopic ultrasound, EUS, guidance. Thus, sampling may be performed as a EUS-FNA/FNB procedure in a minimally invasive manner, e.g. for acquiring samples in a gastric region of a subject.

BRIEF DESCRIPTION OF DRAWINGS

The invention is now described, by way of example, with reference to the accompanying drawings, in which.

DESCRIPTION OF EMBODIMENTS

Figure 1:
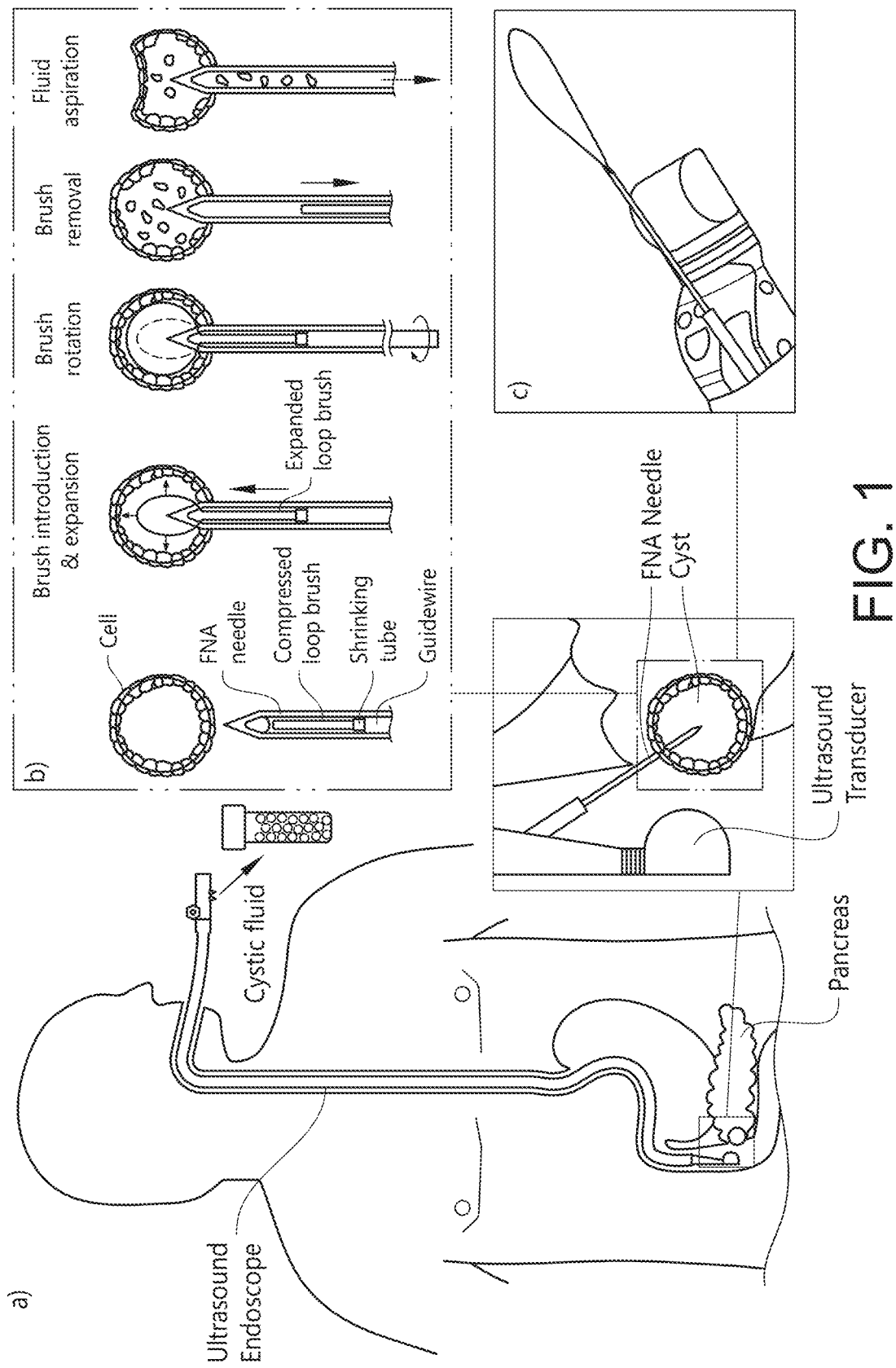
FIG. 1 shows an endoscopic ultrasound guided fine-needle aspiration (EUS-FNA) pathway towards a cyst in the pancreas used by a device according to one embodiment of the present disclosure, different steps of operating the device as well as the device in conjunction with EUS-FNA outside the human body.

In the following, a detailed description of a device according to the present disclosure is presented. In the drawing figures, like reference numerals designate identical or corresponding elements throughout the several figures. It will be appreciated that these figures are for illustration only and are not in any way restricting the scope of the invention.

In the context of the present disclosure, it is understood that the terms "distal" and "distally" refer to a position or direction (furthest) away from the operator when using the device according to the present disclosure. Correspondingly, the terms "proximal" and "proximally" refer to a position or direction closest to or towards the operator when using the device according to the present disclosure.

Referring now to FIG. 1, in drawing a) there is shown a schematic view of an endoscopic ultrasound guided fine-needle aspiration/biopsy (EUS-FNA/FNB) procedure in accordance with to current practice. An endoscope is inserted through the patient mouth, esophagus, stomach, small bowel (duodenum) to reach the pancreas, and when a cyst is located by the ultrasound transducer, the operator inserts a 22G needle into the cyst. However, other organs or regions of interest may be targeted, and the endoscope may be inserted through the colon, anus or rectum. Other gauges of the needle are also foreseen, depending on the procedure.

In drawing b) of FIG. 1, steps of a procedure for improving cell yield are shown. A flexible member in the form of a loop brush, initially located inside the 22G needle, is pushed into the cyst where it conforms to the inner cavity. Rotating the elongated member causes the loop brush to rotate and abrade cells from the cystic wall, causing their release into the cystic fluid. Next, the flexible member is retracted from the lumen of the needle and the cystic fluid is aspirated through the needle and collected for downstream cytology/pathology or biochemistry, molecular or genetic analyses.

To verify the mechanical robustness of the device, stress tests were performed and showed no restraints on loop brush movement, when introducing, rotating and removing a loop brush with a 1200 mm long elongated member through a needle up to 100 times. Photograph c) of FIG. 1 shows a distal end of the endoscope, including the needle and the loop brush.

Pull tests of the flexible member show that mechanical failure occurs at an ultimate force at rupture above 3 N, which is of similar order of magnitude as that for a straight 50 m Nitinol wire (SI5). The level of mechanical stress during in vivo operation remains several orders of magnitude below this ultimate strength.

Figure 2:
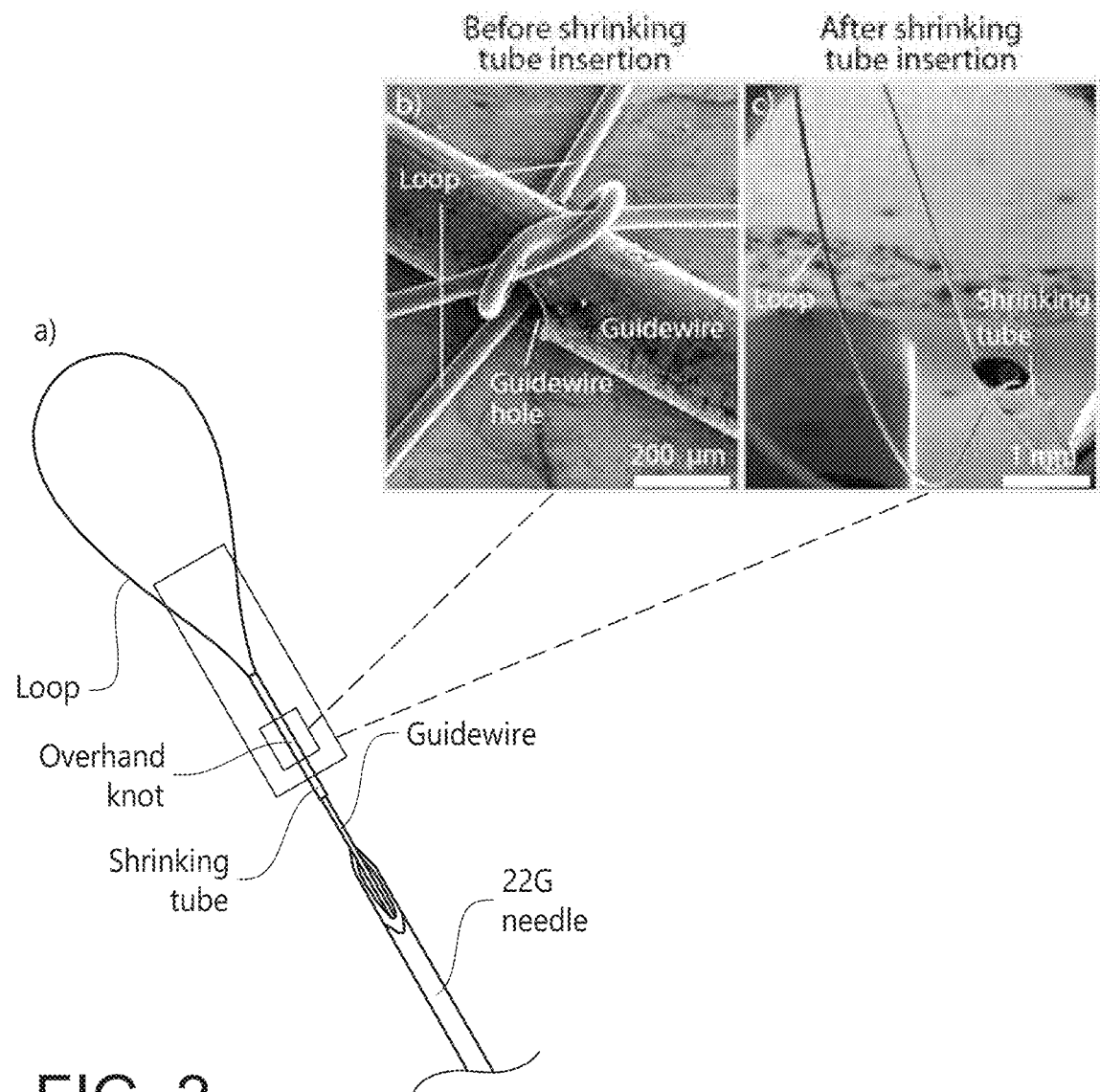
FIG. 2 shows a photograph of a device according to one embodiment of the present disclosure exiting a 22G needle, as well as scanning electron microscope (SEM) images of a mounting interface in the form of a knot before and after placement of a heat shrinking tube.

Referring now to FIG. 2, there is shown a device according to one embodiment of the present disclosure. Photograph a) of FIG. 2 illustrates the distal end of the device, wherein the flexible member in the form of a loop is arranged at the distal end of the elongated member, here referred to as a guidewire. The flexible member consists of a 50 μm thin Nitinol wire shaped in a 1 cm diameter loop. This loop is fixated to a 280 μm thick Nitinol elongated member by an overhand knot as shown in scanning electron microscope (SEM) photograph b) of FIG. 2. The Nitinol wire is knotted to the guidewire through a hole therein. The hole may have a diameter than 0.025 mm and smaller than 5 mm, typically smaller than 0.50 mm. The hole may be positioned 1 mm or up to 10 mm away from the distal end of the elongated member.

After knotting, a heat shrinking tube is inserted over the knot and allowed to shrink by application of heat, thereby encasing the knot, as shown in SEM photograph c) of FIG. 2. The heat shrinking tube may have a diameter larger than 0.1 mm and smaller than 12 mm, typically larger than 0.2 mm.

Other means for mounting the flexible member to the elongated member are foreseen within the scope of the present disclosure, including gluing, welding, mechanical interlocking. The mounting interface may be combined with the heat shrinking tube for encasing, or without the heat shrinking tube. In one embodiment, the elongated member and the flexible member is formed integrally as a monolithic structure, i.e. in a single piece.

Figure 3:
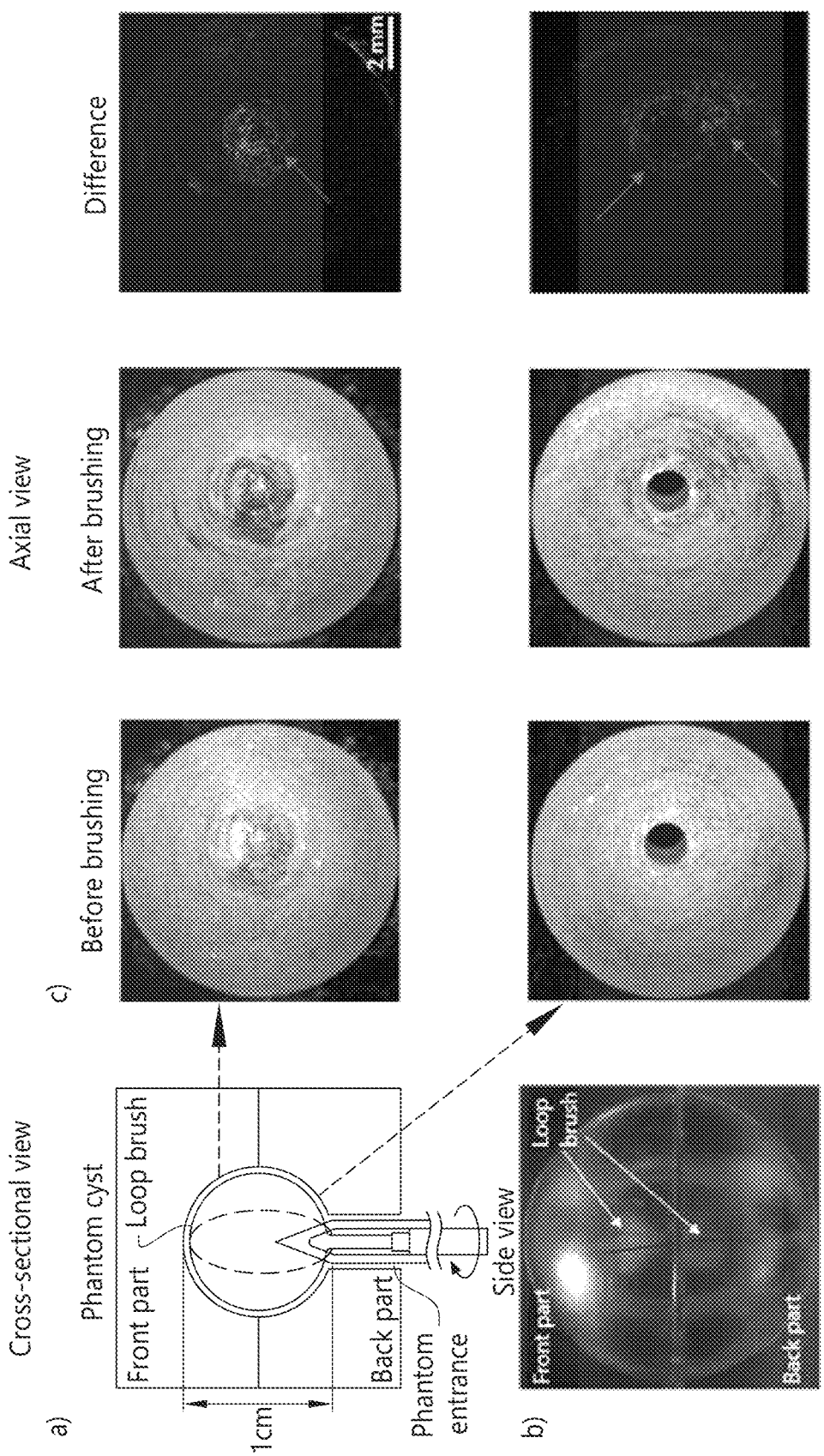
FIG. 3 shows a cross-sectional view of operation of a device according to one embodiment of the present disclosure in the cavity of a cyst phantom, a side view photograph of the cyst phantom with the device inserted, as wells as axial views of front and back parts of the cyst phantom before and after brushing with the device, and the difference therebetween.

Referring now to FIG. 3, the modus operandum of the loop brush in a spherical cavity of an in-vitro cyst phantom was investigated, as shown in drawing a) of FIG. 3. The flexible member was introduced through the lumen of a 22G needle into the cavity and thereafter rotated, as shown in photograph b) of FIG. 3. It was observed that the loop brush conformed to the inner wall of the phantom and showed the flexible member's capability to remove cell-sized talc powder particles from the hard inner wall of the cavity, thus demonstrating the capability of brushing internal 3D curved surfaces, as shown in photographs c) of FIG. 3.

Figure 4:
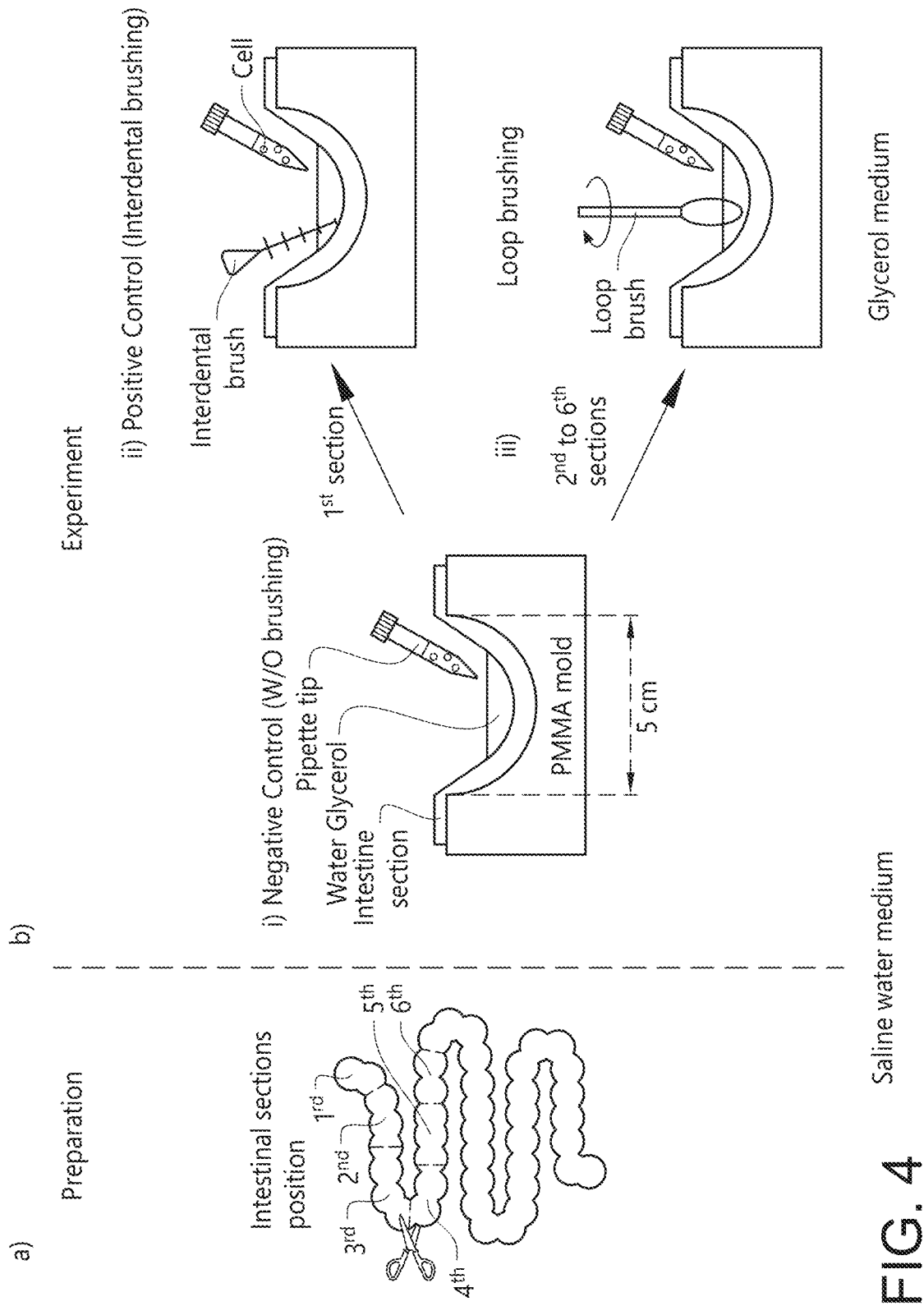
FIG. 4 shows schematic views of ex-vivo testing of a device according to one embodiment of the present disclosure in a porcine small intestine model.

Currently, no animal models of pancreatic cysts exist that are similar to a human cyst size and mimic cell attachment in tissue, which is crucial for the verification of the loop brush functionality. In addition, pancreatic cysts contain fluid of varying viscosity, with higher viscosity indicating higher malignancy. Therefore, an ex-vivo porcine small intestine model was constructed with either saline water or glycerol as the fluid medium. Referring to FIG. 4, the capability of the flexible member to increase the number of cells after brushing was demonstrated. Six intestines, indicated A-F, were used and each intestine was cut into six test sections, indicated 1-6. Drawing a) of FIG. 4 shows a schematic of the sectional cut locations. Drawing b) of FIG. 4 shows cross-sectional schematic of cell harvesting from the model during: i) negative control testing, i.e., subsequent liquid addition and aspiration without brushing; ii) positive control testing, i.e., subsequent liquid addition on the 1st intestinal section, brushing with an interdental brush and liquid aspiration, and; iii) sample testing, i.e., subsequent liquid addition on the 2nd to 6th intestinal sections, brushing with a loop brush and liquid aspiration.

Figure 5A:
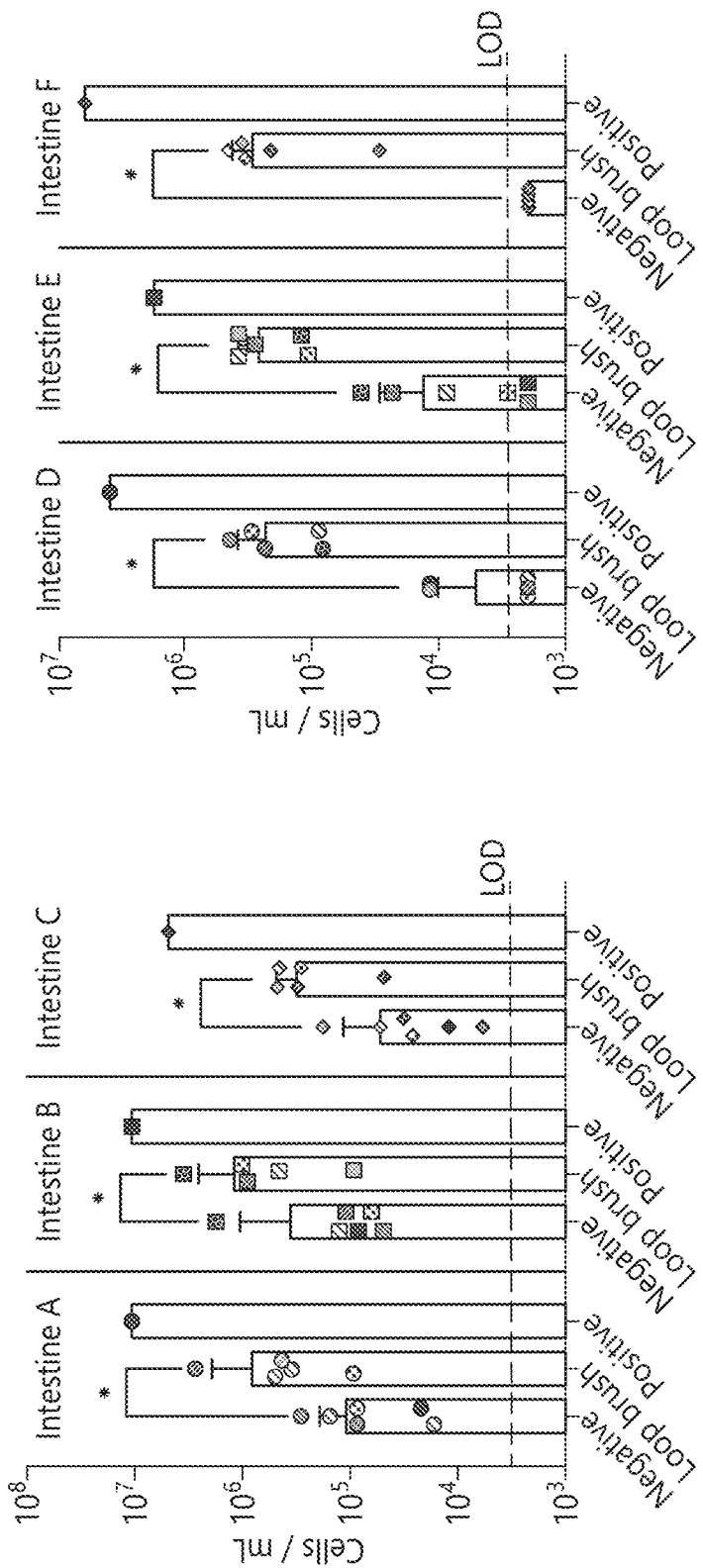
FIGS. 5A and 5B show absolute cell concentrations and brush efficiency from the testing carried out as shown in FIG. 4.

The cell content after fluid removal between loop brushing, negative controls (without brushing) and positive controls (brushing with an interdental brush) was compared. The results are shown in FIGS. 5A, which illustrates absolute cell concentrations, and FIG. 5B, which illustrates brush efficiency, $\eta$. The samples from intestines indicated A-C were filled with saline water, and the samples from intestines indicated D-F were filled with glycerol. Dashed horizontal lines indicate the limit of detection (LOD) of the cell counter. Cell counts below the LOD are represented immediately below the LOD line. Error bars indicate SD. *$P<0.05$. Performing the Wilcoxon paired test on all 15 repetitions of negative control and loop brush, it was found that $P<0.0001$ for both mediums.

The brush efficiency, $\eta$, was defined as the cell concentration ratio of loop brush samples over negative control samples. Where negative control samples contained fewer cells than the limit of detection (LOD) of the cell counter, the LOD value was used instead of the negative control value. All tests showed $\eta>1$. In models with saline water, the average value of $\eta=11$ ($\eta=15$); in models with glycerol content, the average value of $\eta=65$ ($\eta=15$). These results show that the loop brush can remove cells from 3D soft tissue surfaces, after which they can be harvested by aspiration. After loop brushing the cell concentration for saline water and glycerol-filled samples is of a similar order of magnitude, indicating that loop brushing improves cell harvesting in cyst fluid of varying viscosity. A difference in cell content in the negative control measurements between saline water and glycerol filled models was observed. This difference was attributed to the difference in liquid viscosity, leading to more turbulent filling conditions for saline water models and more laminar conditions for glycerol. I.e., filling the model with saline water mixes already released cells in the liquid, whereas glycerol filling maintains such cells close to the intestinal wall.

It was further verified that during typical operation, the force exerted by the flexible member on the tissue was in the approximate range 0.1 mN to 0.7 mN (SI7). The loop brush use was also verified in a model of the endoscope pathway to a cyst, mimicking the curves of the gastrointestinal system. The loop brush was rotated during 1 h at 60 rpm against the lumen of a porcine small intestine model without observed adversities.

Figure 6:
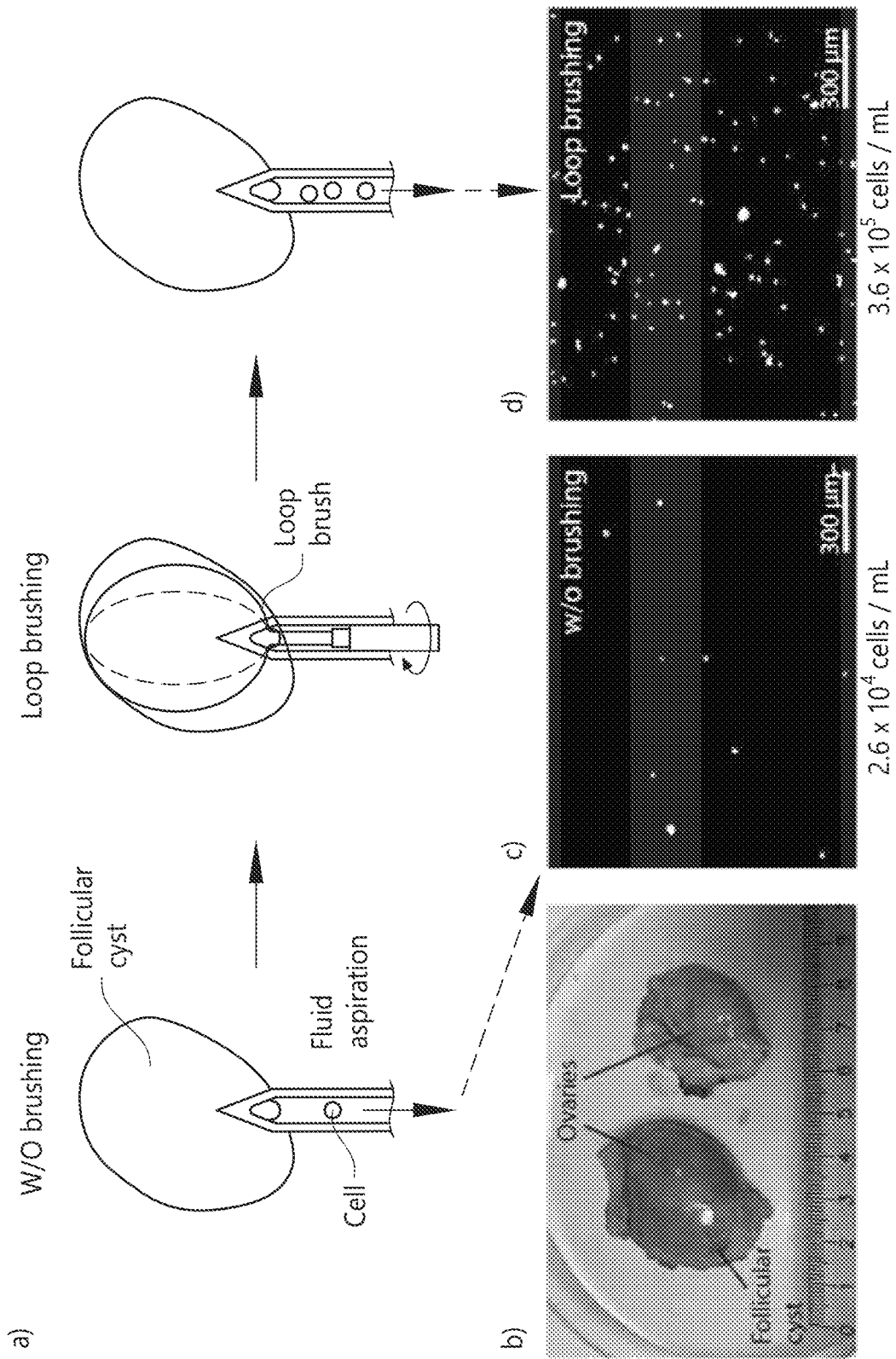
FIG. 6 shows schematic views of ex-vivo testing of a device according to one embodiment of the present disclosure in a bovine follicular cyst as well as cell-counter images without and with brushing.

Referring now to FIG. 6, the capability to increase the number of cells after brushing an ex-vivo bovine follicular cyst model was tested. As shown in drawing a) of FIG. 6, the experimental procedure starts with fluid sampling without brushing (negative control), followed by loop brushing, followed by a second fluid sampling. Photograph b) of FIG. 6 shows cow ovaries with and without follicular cysts. Photographs c) and d) of FIG. 6 show color-enhanced cell counter images for the negative control sample (c) and the loop brush sample (d) and their corresponding cell counts.

Loop brushing increased the cell concentration at least 10-fold compared to the negative control. The presence of cell clusters after brushing did not readily allow counting all cells in the sample, resulting in this efficiency estimate being conservative. These results show that the flexible member can be successfully operated inside a cyst through the lumen of a 22G needle and is capable of brushing and dispersing cells in the liquid environment of a cyst. The capability of the flexible member to gently abrade and disperse cells in more than one type of tissue indicates its potential for the successful operation during pancreatic adenocarcinoma diagnostics.

Current results demonstrate the functionality of the flexible member in the gastrointestinal model, mechanical robustness, simple operation procedure and low force of the flexible member on the tissue and show its compatibility with current EUS-FNA procedures. Future research should aim to evaluate safety of the procedure, specifically with respect to potential damage to the surrounding tissue, and brushing in cysts with septa, i.e., wall structures that separate cystic cavities into two or more compartments.

Figure 7:
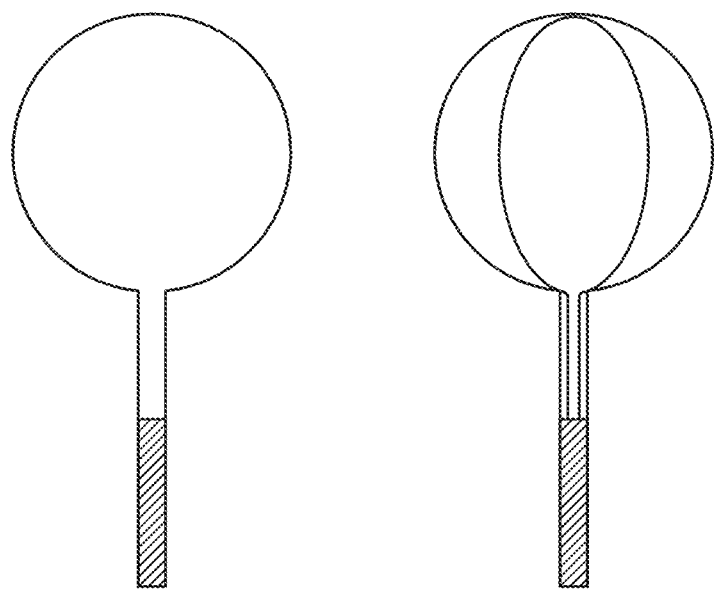
FIG. 7 shows four embodiments of a flexible member arranged at a distal end of the elongated member according to the present disclosure.
Figure 7:
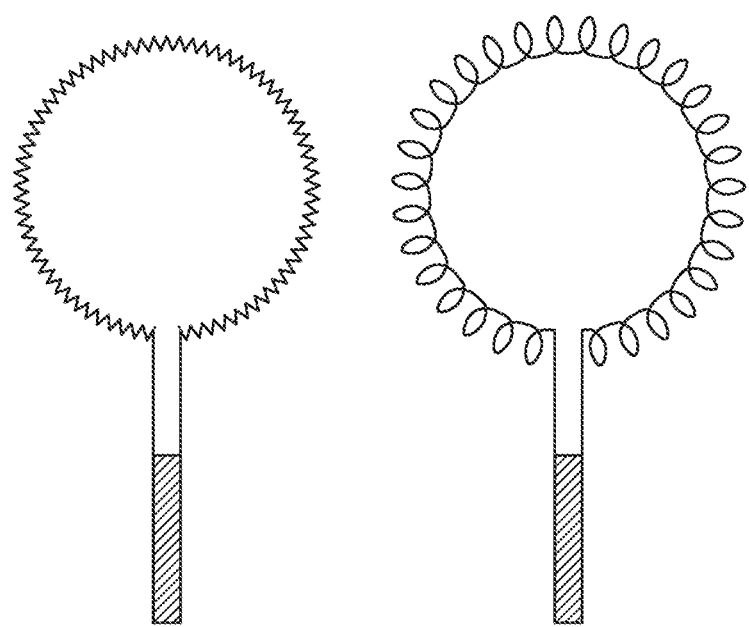

Referring now to FIG. 7, there is shown four embodiments of a loop-shaped flexible member according to the present disclosure. The flexible member is arranged at a distal end of the elongated member. The elongated member may have a diameter larger than 0.1 mm and smaller than 12 mm, typically larger than 0.2 mm. The elongated member may be up to 2 m long and as short as 1 cm, typically larger than 3 cm. In operation, the elongated member may be used to guide the flexible member. For instance, the flexible member may be introduced into, rotated inside, and removed from a cavity upon advancement, rotation, and retraction, respectively, of the elongated member in the needle lumen. The elongated member may be maneuvered by hand or by a mechanical/robotic device. The maneuvering may be carried out on site or remotely.

The flexible member may have a diameter larger than 0.025 mm and smaller than 4 mm, typically smaller than 0.5 mm, more preferably smaller than 0.21 mm. The diameter of the loop may be larger than 1 mm, typically larger than 2 mm, and smaller than 8 cm, typically smaller than 3 cm.

In a first embodiment, the flexible member comprises a single loop, which is substantially circular in the expanded configuration when not constrained in the lumen of a needle or catheter. An exemplary needle may have an inner diameter larger than 0.1 mm and smaller than 6 mm, typically smaller than 5.5 mm. An exemplary catheter may have an inner diameter larger than 0.33 mm and smaller than 12 mm, typically smaller than 9 mm. In a second embodiment, the flexible member comprises more than one loops, e.g. two loops as shown here. In a third embodiment, the flexible member comprises at least one jagged portion, resulting in a plurality of teeth or points in a zigzag pattern. The jagged edge of the loop increases the abrasive action of the flexible member against the wall of a cyst or other cavity, thereby increasing the cell yield. The jagged edge may be formed by a macrostructure of the flexible member, e.g. the flexible member is formed with a jagged structure. In a fourth embodiment, the flexible member is coiled into a helical shape and subsequently formed into a loop such that the axis of the helix is substantially parallel to the general extension direction of the flexible member, i.e. the outline of the loop shape.

Figure 8:
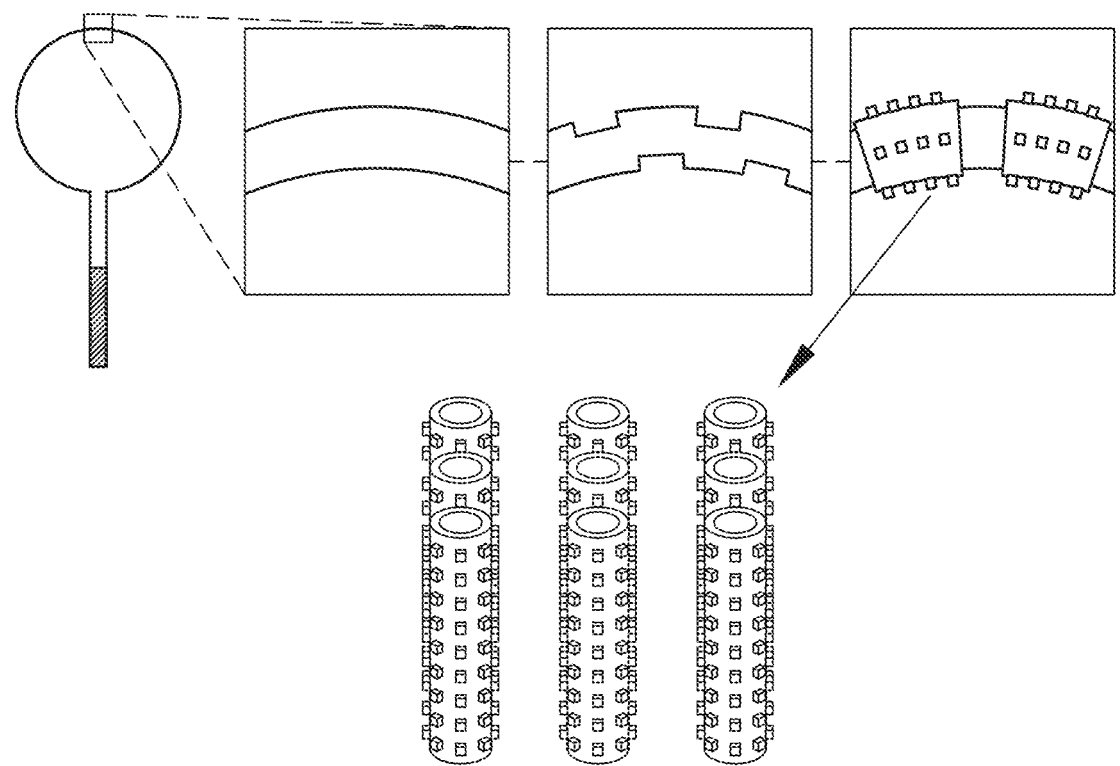
FIG. 8 shows close-up views of a flexible member according to different embodiments of the present disclosure.

Referring now to FIG. 8, there is shown close-up views of the surface of the flexible member according to different embodiments of the present disclosure. In one embodiment, the surface of the flexible member may be substantially smooth as in the upper left embodiment of FIG. 7. In another embodiment, the surface of the flexible member may comprise a microstructure to increase abrasiveness and thus, the cell yield, similar to the lower left embodiment of FIG. 7. The microstructure may be achieved by notches or recesses in the surface of the flexible member as shown in the middle view of FIG. 8. In one embodiment, the microstructure is achieved by means of one or more cylindrical structures having a plurality of protuberances thereon, e.g. studs, and inserted onto the flexible member. The cylindrical structures may be rigid, locally limiting the flexibility of the flexible member. The flexible member can bend in the portions between the cylindrical structures, thus improving the conformal behavior of the flexible member in relation to the tissue wall of the cavity.

Figure 9:
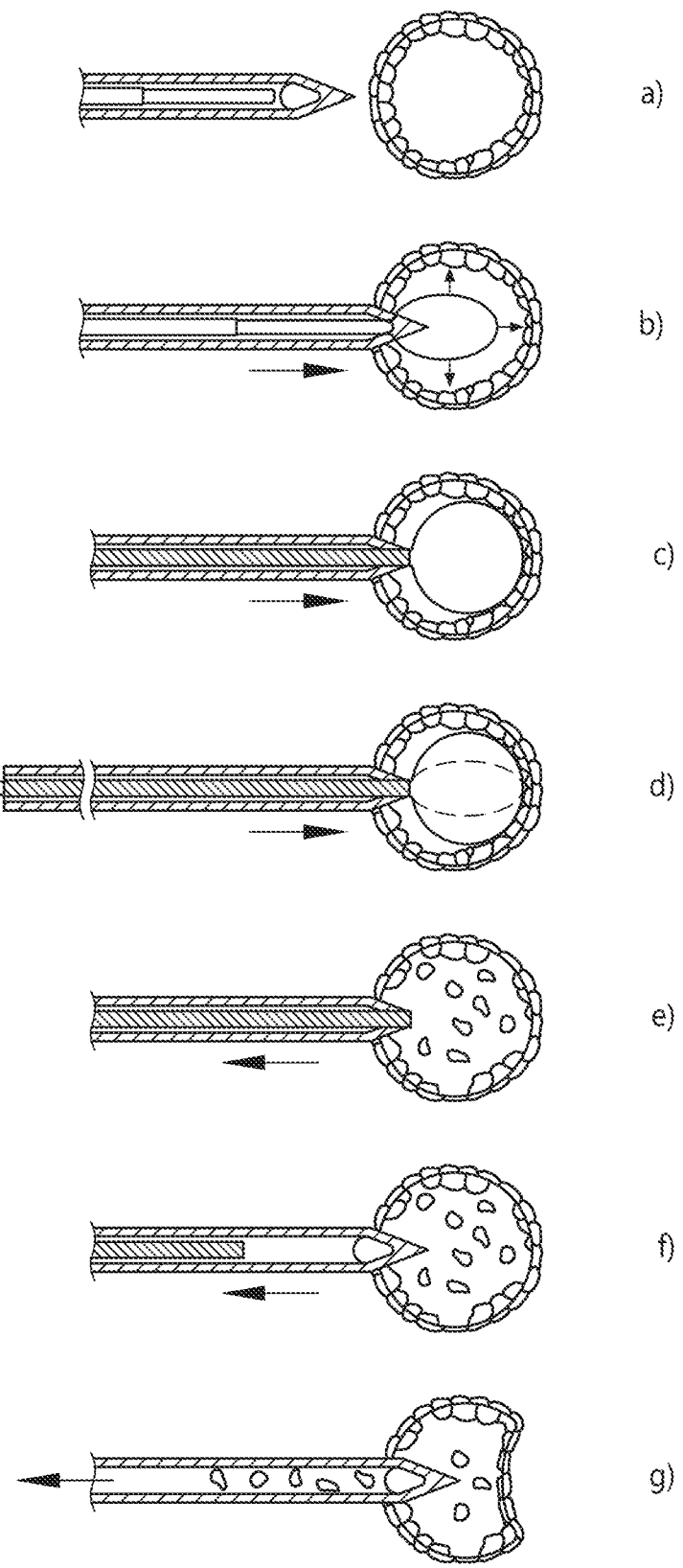
FIG. 9 shows different steps of operating a device according to another embodiment of the present disclosure.

Referring now to FIG. 9, there is shown steps of a procedure for operating the device according to one embodiment of the present disclosure. In step a), a needle comprising a device comprising an elongated member and a flexible member in a constrained configuration inside the lumen of the needle is introduced into a cavity in a subject, e.g. a cyst. In step b), the elongated member is advanced through the lumen of the needle in a distal direction such that the flexible member exits the needle lumen and transitions to the expanded configuration in which the flexible member substantially conforms to the inner geometry of the cyst to contact the inner wall. In step c), a tubular sheath is advanced over the elongated member inside the lumen of the needle until a distal end of the tubular sheath contacts the expanded flexible member. The tubular sheath may be made of a polymer such as polyether, polyamide, polyimide or polytetrafluoroethylene, PTFE, or a metal such as nickel titanium or stainless steel, and protects the flexible member from the sharp facets of the needle. In step d), the elongated member is rotated inside the lumen of the needle which causes the flexible member to rotate inside the cyst and abrade cells from the inner wall. In step e), the elongated member is retracted in a proximal direction such that the flexible member re-enters the needle and transitions to the constrained configuration. At this stage, the tubular sheath is maintained in position beyond the needle tip such that the flexible member does not contact the needle during retraction. In step f), the tubular sheath is retracted in a proximal direction into the lumen of the needle. Finally, in step g), fluid in the cyst is aspirated together with the cells dislodged by the abrading action of the flexible member. The fluid content in the cavity may be naturally excreted by the organism, e.g. urination. The fluid content may be removed by catheterization.

In one embodiment, the aspirated fluid content may be pushed out of the needle lumen by advancing the elongated member and flexible member in a distal direction. In one embodiment, the fluid content may be pushed out of the needle lumen by pushing a wire forward inside the needle, such as e.g. stylet. In one embodiment, the fluid content may be pushed out of the needle lumen by using air or liquid through a syringe. The flexible member may be cut after fluid removal and subsequently used for cytological, pathological, biological, or chemical analysis. The fluid content may be subsequently used for cytological, pathological, biological, or chemical analysis. Said cytological analysis being for example for cell morphology analysis. Said pathological analysis being for example for tissue morphology analysis. Said chemical analysis for example for proteins, glycoproteins, enzymes, DNA, cancer markers, immuno-analysis.

In one embodiment, the surface of the elongated member, the flexible member and/or the tubular sheath may be treated or coated to reduce the coefficient of friction and thereby facilitate advancement, retraction and rotation.

Loop Brush Fabrication

The loop brush in one embodiment consists of three main components: a 280 µm Nitinol elongated member (stylet wire obtained from a Expect™ Slimline EUS-FNA device M00555510, Boston Scientific, USA), a 50 µm Nitinol wire (NiTi #1 wire 0.002"±0.0001" straight annealed light oxide, Fort Wayne Metals, Ireland) knotted to form a loop and a PET medical heat shrinking tube (103-0510, Nordson MEDICAL, USA) with an inner diameter, before shrinking, of 460 µm that protects the knot area.

To fabricate the loop brush, a 150 µm hole was drilled through the distal end of the elongated member. The elongated member was inserted through a 2 cm section of the heat shrink tube without covering the hole. Then the same end of the 50 µm Nitinol wire was passed twice through the hole, forming a loop. The loop was wrapped around a 1 cm in diameter cylinder of ice, and an overhand knot was produced using both ends of the 50 µm Nitinol wire. This ensured the knot position relative to the elongated member and a loop diameter of 1 cm. Then, the ice-cylinder was left at room temperature to melt for 20 min, and the excess wire ends used to facilitate knotting was cut, leaving approximately 1 cm wire ends. Finally, the shrinking tube was manually pushed forward, covering the Nitinol wire ends and the knot, and heated at 70° C. for 30 s to shrink the tube. The shrinking tube had two functions: protect the knot by preventing it from being untied during loop brush movement and to shape the loop form, since a part of the loop wire is held straight inside the shrinking tube, forming a loop shape when outside of the tube.

In-Vitro Cyst Phantom and Brushing Tests

A cyst phantom was created by milling a 2×2×2 cm³ PMMA cube to produce a spherical cavity of 1 cm in diameter. The PMMA cube was made in two parts. A front part contained half of the sphere, and a back part the other half. A 5 mm hole was drilled into the back part to produce the phantom entrance. FIG. 3b shows an image of the brush inside the cyst phantom.

Brushing tests were prepared by applying Scotch® permanent double-sided tape (2346832, Office Depot, Sweden) against the spherical surface for 1 min, removing the tape and placing Dialon® talc powder (7322338361053, Apotea, Sweden) on the surfaces, bonding it to the cyst phantom.

Excess talk powder was removed by clashing both parts 20 times against each other, with the cavities facing each other. Before brushing, the inner cavities were imaged with a Leica M205 C microscope with each part of the cube fixed in a position holder and the cavity facing the microscope. Thereafter, the two parts were assembled with two alignment pins and fixed with a clamp. The loop brush was inserted into a 22G hypodermic needle (4710007040, Henke-Sass Wolf, Germany), that was held in place in front of the phantom entrance. To facilitate testing, the loop brush elongated member was fixed by a wire holder outside the needle. The wire holder was soldered to the axis of a Robotzone 101 rpm @ 12 V DC motor (638194, ServoCity, Sweden).

Brushing the cavity was performed by activating the motor at 60 rpm for 1 min. After brushing, both parts of the sphere were separated and imaged again. Camera settings were maintained constant during all image acquisitions.

To measure the difference before brushing and after brushing, images after brushing were aligned to their respective before brushing image using a Python code (SI4). Following image alignment, all images were converted to 16-bit grayscale, and an image representing the image differences between before and after brushing was obtained for each sphere part. This was performed by using the difference function in ImageJ (version 1.52a, National Institute of Health, USA).

Porcine Intestinal Cyst Model

Porcine small intestines were removed immediately post-mortem by Skovde Slakteri AB (Skovde, Sweden) and bagged in a DMEM (10313021, Thermo Fisher Scientific, Sweden) based medium with 10% FBS (Gibco™ 10270106, Fisher Scientific, Sweden) and 1% Penicillin-Streptomycin (15070063, Thermo Fisher Scientific, Sweden), to prevent tissue decomposition. The intestines were stored at 4° C. until use up to 24 h post-mortem.

For each experiment, the small intestine was cut using a scalpel, separating it into six 8 cm-long segments, starting approximately 3 cm away from the pylorus. These segments were subsequently cut open axially to expose the luminal side of the intestine completely. All exposed pieces were rinsed with tap water for 1 min and simultaneously gently scrubbed manually to remove sustenance remnants. Each intestinal piece was placed in a container with tap water, where the tissue was held until testing within 20 min.

For brushing tests, a hemispherical mold with a radius of 2.5 cm was used to hold the intestinal piece. The mold had five drilled holes of 1 mm in diameter connected to a vacuum line to maintain the intestinal piece in place with the luminal side facing outwards (FIG. 4b)

Tests without brushing (negative controls) were made by placing 300 µL of 0.9% saline water (786-561, G-Biosciences, Sweden) or glycerol (G9012, Sigma-Aldrich, Sweden) on the tissue after fixation in the mold. The liquid was let to rest for 1 min, followed by careful aspiration of 100 µL of liquid using a pipette, during which care was taken not to touch the intestinal wall. This method preceded every loop brushing and positive control experiment and revealed the number of cells naturally shed to the medium by either sample cutting, cleaning, handling, and/or medium placement onto the sample. Thus, each intestine section was subjected to a negative control test prior to loop brushing testing on the same intestinal section. Loop brushing was performed on five out of six of the intestinal sections. Following negative control testing, loop brushing started by adding an additional 100 μL of liquid on the tissue section, thus maintaining liquid volume throughout tests. Positive control brushing was performed on the remaining tissue section, after negative control testing, also starting by adding an additional 100 μL of liquid on the tissue section. An interdental brush (Dentalux, Sweden) was used as positive control brush. This brush was gently pressed against the intestinal lumen followed by an axial back and forth movement in a 0.5 cm2 area at the center of the intestinal piece, without rotation, for 1 min. After brushing, 100 μL of liquid was aspirated once more.

Bovine Follicular Cyst Model

The bovine reproductive system was removed immediately post-mortem by Skovde slakteri and bagged in a DMEM-based medium with 10% FBS and 1% Penicillin-Streptomycin, to prevent tissue decomposition and stored at 4° C. for 24 h before resection.

Figure 5B:
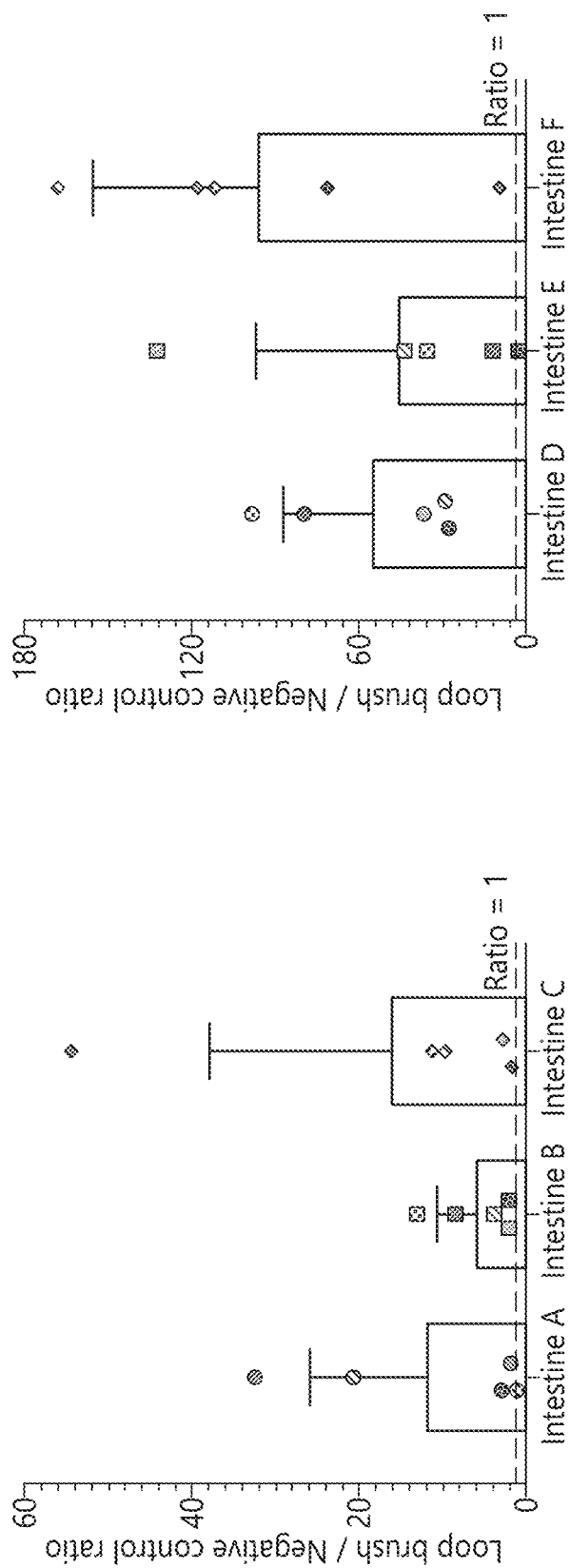

One ovary without, and one containing, a follicular cyst were resected from the bovine reproductive system using a scalpel and fixed in a Petri dish (FIG. 5B). The experimental design is illustrated in FIG. 5A) and proceeded as follows. First, the follicular cyst was punctured, and 1.5 mL of liquid was aspirated using a 22G hypodermic needle and a syringe. Second, the follicular cyst was punctured once more, using a 22G hypodermic needle with a pre-installed loop brush, followed by loop brush introduction, manual rotation for 1 min at approximately 60 rpm, and brush removal. Finally, 1.5 mL of cystic liquid was aspirated through the needle using a syringe. After homogenization, aliquotes of 100 μL of the 1.5 mL samples were removed for further cell analysis.

Liquid Sample Treatment

The aspirated liquid samples were transferred into test tubes (0030120086, Eppendorf, Sweden) and subsequently mixed with 500 μL StemPro™ Accutase™ (A1110501, Thermo Fisher Scientific, Sweden), gently homogenized with a pipette by aspirating and dispensing liquid in 2-s cycles for 30 s, and incubated at 37° C. for 5 min. Samples (except bovine) were then filtered using a 70 μm cell strainer (431751, CorningQR, Netherlands) and centrifuged using a Micro Star 17R centrifuge (VWR, Sweden) at 11000 rpm for 4 min. The supernatant was removed, and a fluorophore solution of saline water with Hoechst 33342 (H3570, Thermo Fisher Scientific, Sweden), in a 0.05% v/v concentration, was added to each sample. Positive controls were mixed with 100 μL of the solution, and negative controls and loop brushing samples were mixed with 50 μL of the solution to accommodate adequate pellet sizes. Finally, samples were wrapped with aluminum foil for 20 min and unwrapped again, in preparation for cell counting.

Cell Counter Analysis

Cell counting was performed with a Countess II FL automated cell counter (Thermo Fisher Scientific, Sweden), coupled with an EVOS™ light cube, DAPI (AMEP4650, Thermo Fisher Scientific, Sweden). All samples were gently homogenized with a pipette and 10 μL of the sample was placed on a Countess™ cell counting chamber slide (C 10228, Thermo Fisher Scientific, Sweden). Intestinal sample cell counting was performed using the DAPI light cube, with the following settings: size between 4-14 μm, brightness between 0-255 a.u., circularity of 0.67, and using autofocus. Follicular cyst sample cell counting was also performed using the DAPI light cube, with: size between 6-29 μm, brightness between 0-255 A.U., circularity of 0.78 and autofocus. Finally, dilution calculations were performed for a final volume of 50 μL, for both intestinal and follicular cyst samples.

Statistical Analysis

Intestinal cell counting results were applied to a one-sided Wilcoxon matched-pairs signed rank test with a significance level of 5%, to test for a statistically significant difference between using or not using the loop brush. This was accomplished using GraphPad Prism 8 software (GraphPad, CA, USA).

CONCLUSIONS

A loop brush designed to acquire cells from the inner wall of pancreatic cysts and hollow cavities in conjunction with EUS-FNA was successfully tested. No adversities were found when introducing, rotating, and removing the loop Brush from a cyst through a 22G needle. The cellular content in fluid retrieved from ex-vivo cyst models before and after brushing with the loop brush was compared. The cell content increased up to 54× when using low-viscous water as fluid in soft tissue soft-like cavities; up to 174× when using high-viscous glycerol, and; at least 10× in cow ovary cysts. The loop brush proves to be a powerful, minimally invasive, and all-around tool capable of operation in conjunction with EUS-FNA and of brushing cells from cysts, in soft and hard-like cyst models and with serous or viscous-like liquids.

Loop brush experiments were conducted with a brush connected to the DC motor resembling the in-vitro cyst phantom testing. The distal end of the brush was gently pressed against the intestinal lumen and rotated at 60 rpm in a 0.5 cm2 area at the center of the intestinal piece, for 1 min. After this, 100 μL of liquid was aspirated with a pipette. Between every experiment, the used intestinal section was discarded and the mold was cleaned with ethanol and scrubbed with cleanroom paper.

Preferred embodiments of a device for detaching cells or tissue from a cavity in a subject according to the present disclosure has been described. However, the person skilled in the art realizes that these can be varied within the scope of the appended claims without departing from the inventive idea.

All the described alternative embodiments above or parts of an embodiment can be freely combined without departing from the inventive idea as long as the combination is not contradictory.

What is claimed is:

1. A sampling device for performing fine-needle aspiration (FNA) or fine-needle biopsy (FNB) from a cavity in a subject, the sampling device comprising:
    a hollow needle;
    an elongated member movably arranged inside a lumen of the needle;
    a flexible member arranged at a distal end of the elongated member, wherein the flexible member has a first, constrained configuration within the lumen of the needle and, following advancement of the elongated member in the needle, the flexible member has a second, expanded configuration outside said lumen, wherein the flexible member is arranged to form a loop in the expanded configuration, the loop extending in a plane that is parallel to an axis of the elongated member; and
    a tubular sheath arranged outside the elongated member and configured to be moved along the elongated member inside the lumen of the needle so that a distal end of the tubular sheath contacts the loop of the expanded configuration outside the lumen of the needle.

2. The sampling device according to claim 1, wherein the flexible member is a superelastic wire.

3. The sampling device according to claim 2, wherein the flexible member is made of a shape-memory alloy.

4. The sampling device according to claim 1, wherein at least a portion of the flexible member has a substantially helical shape in which the axis of the helix is substantially parallel to a general extension direction of the flexible member.

5. The sampling device according to claim 1, wherein at least a portion of the flexible member has a jagged structure.

6. The sampling device according to claim 5, wherein the jagged structure is achieved by means of a microstructure machined or arranged on a surface of the flexible member.

7. The sampling device according to claim 1, wherein the elongated member and the flexible member are integrally formed as a monolithic structure, wherein a diameter of the flexible member is smaller than a diameter of the elongated member.

8. The sampling device according to claim 1, wherein the elongated member comprises a mounting interface at the distal end thereof, and the flexible member is attached to the elongated member by means of the mounting interface.

9. The sampling device according to claim 8, wherein the mounting interface comprises at least one hole for fastening the flexible member to the elongated member, a welding seam, a gluing seam or a mechanical interlocking mechanism between the elongated member and the flexible member, or combinations thereof.

10. The sampling device according to claim 9, wherein the mounting interface is covered with a heat shrinking tube.

11. The sampling device according to claim 1, wherein the tubular sheath is made of a polymer selected from polyether, polyamide, polyimide or polytetrafluoroethylene (PTFE) or a metal selected from nickel titanium or stainless steel.

12. The sampling device according to claim 1, wherein the elongated member and/or the flexible member is surface treated or coated to reduce their coefficient of friction.

13. The sampling device according to claim 1, wherein the loop is substantially circular in the second, expanded configuration.

14. The sampling device according to claim 1, wherein the loop in the expanded configuration is configured to engage an inner geometry of the cavity and adopt a shape that conforms to a majority of a section of the inner geometry of the cavity, wherein the loop is further configured to rotate about the axis of the elongated member and detach cells or tissue from the cavity during rotation of the loop.

15. A method for performing fine-needle aspiration (FNA) or fine-needle biopsy (FNB) to sample cells or tissue from a cavity in a subject, the method comprising:
    providing a device that includes:
        a hollow needle,
        an elongated member arranged to be moved within a lumen of the needle,
        a flexible member arranged at a distal end of the elongated member, wherein the flexible member has a first, constrained configuration within the lumen of the needle and, following advancement of the elongated member in the needle or catheter, the flexible member has a second, expanded configuration outside said lumen, wherein the flexible member is arranged to form a loop in the expanded configuration, the loop extending in a plane that is parallel to an axis of the elongated member, and
        a tubular sheath arranged outside the elongated member and configured to be moved along the elongated member inside the lumen of the needle so that a distal end of the tubular sheath contacts the loop of the expanded configuration outside the lumen of the needle;
    introducing the needle into the cavity in the subject;
    advancing the elongated member through the lumen of the needle in a distal direction such that the flexible member protrudes from a distal tip of the needle and expands to the expanded configuration, the flexible member forming the loop in the expanded configuration so as to come into contact with an inner wall of the cavity;
    advancing the tubular sheath through the needle such that the distal end of the tubular sheath exits the distal tip of the needle and contacts the loop of the expanded flexible member;
    rotating the elongated member such that the loop of the expanded flexible member scrapes the inner wall of the cavity;
    retracting the elongated member into the lumen of the needle such that the flexible member is brought to the first, constrained configuration and re-enters the distal tip of the needle;
    retracting the tubular sheath into the needle;
    aspirating fluid from the cavity through the lumen of the needle; and
    retracting the needle from the cavity.

16. The method according to claim 15, wherein introducing the needle into the cavity in the subject comprises introducing the needle into the cavity in the subject using endoscopic ultrasound (EUS) guidance.

17. The method according to claim 15, further comprising:
    removing the aspirated fluid from the lumen of the needle by one or more of:
        advancing the elongated member and the flexible member in the distal direction;
        inserting a wire inside the lumen of the needle; or
        injecting air or liquid into the lumen of the needle using a syringe.

18. The method according to claim 15, wherein the providing the device comprises:
    forming microstructures in or on a surface of the flexible member; and/or
    forming integral, as a monolithic structure, the elongated member and the flexible member.

19. The method according to claim 15, wherein the providing the device comprises providing the device that includes: the loop in the expanded configuration is configured to engage an inner geometry of the cavity and adopt a shape that conforms to a majority of a section of the inner geometry of the cavity, wherein the loop is further configured to rotate about the axis of the elongated member and detach cells or tissue from the cavity during rotation of the loop.

20. The method according to claim 15, wherein the elongated member comprises a mounting interface at the distal end thereof, and wherein the providing the device comprises attaching the flexible member to the elongated member by means of the mounting interface.

21. The method according to claim 20, further comprising:
    covering the mounting interface with a heat shrinking tube.

* * * * *